United States Patent [19]

Puckette

[11] Patent Number: 4,954,227
[45] Date of Patent: Sep. 4, 1990

[54] PREPARATION OF BIDENTATE LIGANDS

[75] Inventor: Thomas A. Puckette, Longview, Tex.

[73] Assignee: Eastman Kodak Company, Rochester, N.Y.

[21] Appl. No.: 383,697

[22] Filed: Jul. 24, 1989

Related U.S. Application Data

[62] Division of Ser. No. 118,573, Nov. 9, 1987, Pat. No. 4,879,008.

[51] Int. Cl.$^5$ .............................................. C25C 3/00
[52] U.S. Cl. .................................. 204/72; 204/73 R; 204/78; 556/70; 556/71; 568/13; 568/14; 568/15; 568/17; 570/185; 570/191; 570/196; 564/384; 564/386
[58] Field of Search ...................... 556/70, 71; 568/13, 568/14, 15, 17; 570/185, 191, 196; 564/384, 386; 204/72, 73 R, 78

[56] References Cited

PUBLICATIONS

Gilman, H., ed., *Organic Chemistry: An Advanced Treatise*, vol. 1, 2nd Ed., John Wiley & Sons, Inc., New York, N.Y., ©1943, pp. 562-563.

*Primary Examiner*—Patrick P. Garvin
*Assistant Examiner*—George R. Fourson
*Attorney, Agent, or Firm*—J. Frederick Thomsen; S. E. Reiter; William P. Heath, Jr.

[57] ABSTRACT

A process is disclosed for preparing bidentate ligands of the formula:

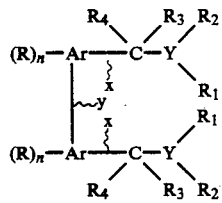

wherein:

each AR is independently selected from aromatic ring compounds having 6 up to 14 carbon atoms, e.g., phenyl, naphthyl, phenanthryl and anthracenyl;

the x bonds and the y bonds are attached to adjacent carbon atoms on the ring structures;

each R, when present as a substituent, is independently selected from alkyl, alkoxy, aryloxy, aryl, aralkyl, alkaryl, alkoxyalkyl, cycloaliphatic, halogen, alkanoyl, alkanoyloxy, alkoxycarbonyl, carboxyl, cyano or formyl radicals;

n is a whole number in the range of 0–4 were Ar is phenyl; 0–6 where Ar is naphthyl; and 0–8 where Ar is phenanthryl or anthracenyl;

each $R_1$ and $R_2$ is independently selected from alkyl, aryl, aralkyl, alkaryl or cycloaliphatic radicals, or substituted derivatives thereof;

each $R_3$ and $R_4$ is independently selected from hydrogen and the $R_1$ substituents;

each of the above alkyl groups or moieties is straight or branched chain of 1-20 carbons;

each aryl group contains 6–10 rings carbons;

each cycloaliphatic group contains from 4–8 ring carbons;

each Y is independently selected from the elements, N, P, As, Sb and Bi; and substituted derivatives include ethers, amines, amides, sulfonic acids, esters, hydroxyl groups and alkoxy groups.

The invention process comprises coupling two molecules of a reactant of the formula

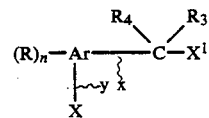

by maintaining a redox reaction system comprising said reactant, a polar aprotic solvent, a nickel compound and a reducing agent at a temperature and for a time sufficient to form the desired bidentate ligand.

11 Claims, No Drawings

PREPARATION OF BIDENTATE LIGANDS

This is a divisional of copending application Ser. No. 118,573, filed on Nov. 9, 1987, now U.S. Pat. No. 4,879,008.

This invention relates to the preparation of bidentate ligands which are useful, for example, in the formation of low pressure hydroformylation catalysts.

BACKGROUND OF THE INVENTION

Bidente ligands have recently been shown to be very effective for the preparation of organometallic catalysts, such as for example, low pressure hydroformylation catalysts wherein the bidentate ligands are coordinated with rhodium. While a variety of bidentate ligands are useful for such chemical conversions as hydroformylation, their synthesis is often difficult, involving numerous reaction steps, one or more of which give low product yields. The net result is that the target bidentate ligands are obtained in low overall yields and are expensive to prepare.

In order for bidentate ligands such as:

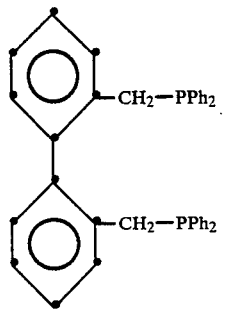

to come into more widespread use, efficient means for the preparation of such bidentate ligands will need to be developed.

OBJECTS OF THE INVENTION

It is, therefore, an object of the present invention to develop improved methods for the preparation of bis(-dihydrocarbylphosphinomethyl)-biphenyl-type bidentate ligands.

This and other objects will become apparent from inspection of the detailed description and claims which follow.

STATEMENT OF THE INVENTION

In accordance with the present invention, we have discovered that bis(dihydrocarbylphosphino-methyl)-biphenyl-type compounds can be prepared by the reductive coupling of two molecules of a halogen substituted aromatic phosphine. The resulting diphosphine compounds are useful as bidentate ligands in combination with a wide variety of active metal species. For example, when employed in combination with rhodium, the bis(dihydrocarbylphosphinomethyl)-biphenyl-type compounds prepared in accordance with the present invention are useful as components of low pressure hydroformylation processes. Such catalyst systems produce unusually high proportions of normal (or unbranched) aldehydes from α-olefins, e.g., n-butyraldehyde from propylene.

DETAILED DESCRIPTION OF THE INVENTION

In accordance with the present invention, there is provided a process for preparing a bidentate ligand of the formula:

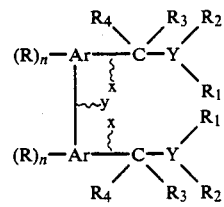

wherein:

each Ar is independently selected from aromatic ring compounds having 6 up to 14 carbon atoms, e.g., phenyl, naphthyl, phenanthryl and anthracenyl;

the x bonds and the y bonds are attached to adjacent carbon atoms on the ring structures;

each R, when present as a substituent, is independently selected from alkyl, alkoxy, aryloxy, aryl, aralkyl, alkaryl, alkoxyalkyl, cycloaliphatic, halogen, alkanoyl, alkanoyloxy, alkoxycarbonyl, carboxyl, cyano or formyl radicals;

n is a whole number in the range of 0-4 were Ar is phenyl; 0-6 where Ar is naphthyl; and 0-8 where Ar is phenanthryl or anthracenyl;

each $R_1$ and $R_2$ is independently selected from alkyl, aryl, aralkyl, alkaryl or cycloaliphatic radicals, or substituted derivatives thereof;

each $R_3$ and $R_4$ is independently selected from hydrogen and the $R_1$ substituents;

each of the above alkyl groups or moieties is straight or branched chain of 1-20 carbons;

each aryl group contains 6-10 rings carbons;

each cycloaliphatic group contains from 4-8 ring carbons;

each Y is independently selected from the elements N, P, As, Sb and Bi; and substituted derivatives include ethers, amines, amides, sulfonic acids, esters, hydroxyl groups and alkoxy groups.

The invention process comprises maintaining a redox reaction system comprising a reactant of the formula:

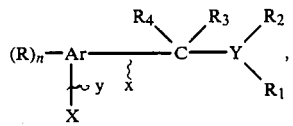

a polar, aprotic solvent, a nickel compound, and a reducing agent at a temperature suitable for coupling for a time sufficient to form the desired bidentate ligand. It is of note that no other reaction components are required to accomplish the desired coupling reaction, e.g., no added ligand is required for the nickel component.

In a particular embodiment of the present invention, the bidentate ligands prepared in accordance with the invention process are compounds of the formula:

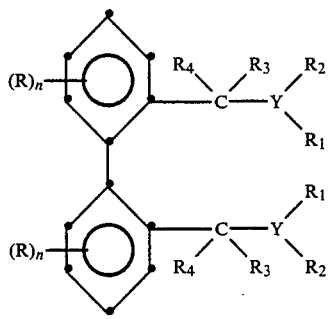

wherein:

n is 0-4;

each R is independently selected from alkyl, alkoxy, aryloxy, aryl, aralkyl, alkaryl, alkoxyalkyl, cycloaliphatic, halogen, alkanoyl, alkanoyloxy, alkoxycarbonyl, cyano, carboxyl or formyl radicals;

each $R_1$ and $R_2$ is independently selected from alkyl, aryl, aralkyl, alkaryl or cycloaliphatic radicals, or substituted derivatives thereof;

each $R_3$ and $R_4$ is independently selected from hydrogen and the $R_1$ substituents;

each of the above alkyl groups or moieties is straight or branched chain of 1-20 carbons, each aryl group contains 6-10 ring carbons, and each cycloaliphatic group contains from 4-8 ring carbons;

each Y is independently selected from the elements N, P, As, Sb and Bi, with P being preferred; and substituted derivatives include ethers, amines, amides, sulfonic acids, esters, hydroxyl groups and alkoxy groups.

In another particular embodiment of the present invention the bidentate ligands prepared in accordance with the invention process are compounds of the general formula:

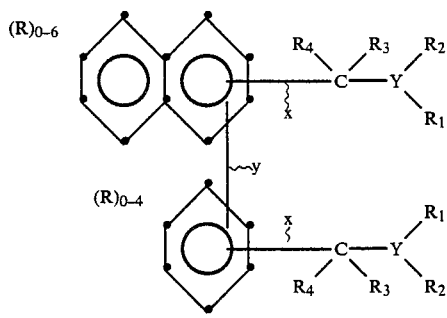

wherein:

the x bonds and the y bonds are attached to adjacent carbon atoms on the ring structures;

each R when present as a substituent is independently selected from alkyl, alkoxy, aryloxy, aryl, aralkyl, alkaryl, alkoxyalkyl, cycloaliphatic, halogen, alkanoyl, alkanoyloxy, alkoxycarbonyl, cyano, carboxyl, or formyl radicals;

each $R_1$ and $R_2$ is independently selected from alkyl, aryl, aralkyl, alkaryl or cycloaliphatic radicals, or substituted derivatives thereof;

each $R_3$ and $R_4$ is independently selected from hydrogen and the $R_1$ substituents;

each of the above alkyl groups or moieties is straight or branched chain of 1-20 carbons, preferably 1-8 carbons, each aryl group contains 6-10 ring carbons, and each cycloaliphatic group contains from 4-8 ring carbons;

each Y is independently selected from the elements N, P, As, Sb and Bi, with P being preferred; and substituted derivatives include ethers, amines, amides, sulfonic acids, esters, hydroxyl groups and alkoxy groups.

In yet another particular embodiment of the present invention, the bidentate ligands prepared in accordance with the invention process are compounds of the general formula:

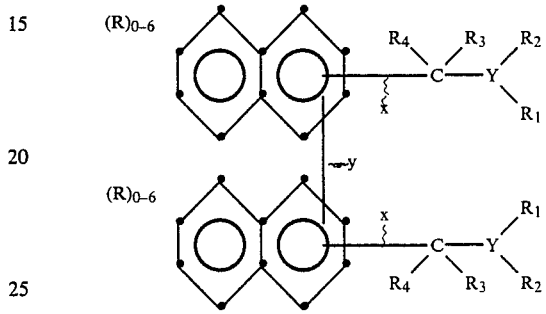

wherein:

the x bonds and the y bonds are attached to adjacent carbon atoms on the ring structure;

each R when present as a substituent is independently selected from alkyl, alkoxy, aryloxy, aryl, aralkyl, alkaryl, alkoxyalkyl, cycloaliphatic, halogen, alkanoyl, alkanoyloxy, alkoxycarbonyl, cyano, carboxyl, or formyl radicals;

each $R_1$ and $R_2$ is independently selected from alkyl, aryl, aralkyl, alkaryl or cycloaliphatic radicals, or substituted derivatives thereof;

each $R_3$ and $R_4$ is independently selected from hydrogen and the $R_1$ substituents;

each of the above alkyl groups or moieties is straight or branched chain of 1-20 carbons, preferably 1-8 carbons, each aryl group contains 6-10 ring carbons, and each cycloaliphatic group contains from 4-8 ring carbons;

each Y is independently selected from the elements N, P, As, Sb and Bi, with P being preferred; and substituted derivatives include ethers, amines, amides, sulfonic acids, esters, hydroxyl groups and alkoxy groups.

Especially preferred compounds which can be prepared in accordance with the invention process include:

2,2'-bis(diphenylphosphinomethyl)-1,1'-biphenyl (hereinafter, BISBI);

2,2'-bis(dibenzylphosphinomethyl)-1,1'-biphenyl;

2,2'-bis(phenylbenzylphosphinomethyl)-1,1-biphenyl;

2,2'-bis(diisobutylphosphinomethyl)-1,1'-biphenyl;

2-(diphenylphosphinomethyl)-1-[2-(diphenyl-phosphinomethyl)phenyl]naphthalene; and 2,2'-bis(diphenylphosphinomethyl)-1,1'-binaphthyl.

The reductive coupling reaction is generally carried out at a temperature in the range of about 50° C. and 200° C., preferably between about 110° C. and about 140° C.

Reaction pressure employed for the reductive coupling is not critical. Typically, the reaction is carried out at atmospheric pressure, although higher and lower pressures can be employed.

The reducing agent metal is generally present with respect to the nickel compound in a molar ratio in the range of about 5/1 up to 1,000/1, preferably in the range of about 10/1 up to 400/1, and most preferably from about 25/1 to about 100/1, although higher or lower ratios may be used. Very low ratios, however, will typically result in incomplete reaction and low yield.

It is also preferred that the ratio of polar, aprotic solvent (in mL) with respect to the reactant (halobenzyl phosphine; in moles) be in the range of about 100/1 up to 10,000/1, and most preferably in the range of about 200/1 up to 2,000/1. The molar ratio of nickel compound with respect to the reactant (halobenzyl phosphine) should be in range of about 2/1 up to 100/1, preferably in the range of about 5/1 up to 40/1, and most preferably in the range of about 10/1 up to 30/1. While higher or lower ratios may be used, there are no practical reasons therefor.

Solvents suitable for use in the practice of the present invention are polar (i.e., high dipole moment), aprotic solvents, such as, for example, dimethylformamide, dimethylacetamide, N-methyl pyrrolidone, N,N-dimethyl benzamide, N-methyl piperidone, benzonitrile, and the like.

A wide range of nickel compounds are suitable for use in the practice of the present invention, so long as the nickel compounds employed are essentially water-free. The nickel (II) halide salts are a convenient source of nickel as such compounds are readily available in anhydrous form. Those of skill in the art recognize that a wide variety of other nickel compounds can be used, e.g., nickel nitrates, sulfates, phosphates, oxides, carbonates, carboxylates, acetylacetonate and the like, as well as Ni(O) complexes such as, for example, bis(1,5-cyclooctadienyl)nickel(O), nickel(O) tetracarbonyl, and the like.

The nickel (II) halides are presently preferred because of their ready availability in anhydrous form, and because the presence of halides in the reaction mixture appears to promote the coupling reaction.

When halide-free nickel compounds are employed, it may be desirable to provide a source of halide to the reaction mixture. A convenient supplemental source of halide is an alkali metal halide, preferably as the sodium or potassium halide. Up to about 200 moles of halide per mole of nickel will impart a beneficial effect on the coupling reaction, with about 10 up to 80 moles of halide per mole of nickel being preferred. In a most preferred embodiment, about 20 up to 50 moles of halide per mole of nickel will be added to the coupling reaction mixture.

The reducing agent employed in the invention process will have a sufficient reducing potential to promote the reduction of Ni(II) to Ni(O). Thus, any element with an electromotive force (EMF) more negative than −0.25 V could be employed. Elements which satisfy this criterion include calcium, zinc, magnesium, manganese, sodium and lithium. Presently preferred elements are zinc, magnesium and manganese.

While the reducing agent employed in the practice of the present invention is preferably internal to the reaction system, those of skill in the art recognize that the known external reducing agent, an electrochemical cell, can also be used. In such a system, conventional E.M.F. values for the particular concentrations of the aryl halide reactant to be coupled, nickel compound and electrolyte, e.g., tetrabutylphosphonium bromide, lithium bromide, etc., can be employed. The determinations of such E.M.F., component concentrations, bath size and the like can readily be carried out by those skilled in the art.

A typical useful electrochemical cell is

Undivided cells may also be used. In carrying out such an electrochemical reaction in the laboratory, the following parameters are exemplary for coupling 2-chlorobenzyldiphenylphosphine (2-CBDP):

| | |
|---|---|
| Bath size | 1.0 L |
| Dimethylformamide | 500 mL |
| 2-CBDP | 0.4 moles |
| $NiCl_2$ | 0.02 moles |
| LiBr | 0.3 N |
| E.M.F. | −1.5 volts (relative to the Saturated Calomel Electrode) |

It is preferred to agitate the bath in known manner and to maintain the electrochemical reaction mixture at a temperature suitable for producing the coupled product. The temperature of the electrochemical reaction mixture is preferably maintained in the range of about 50° C. to 200° C., and most preferably in the range of about 110° C. up to 140° C.

In the reductive coupling reaction, the solvent employed is preferably dimethylformamide or dimethylacetamide, or mixtures thereof; the nickel compound employed is preferably nickel chloride or nickel bromide, or mixtures thereof; and the reducing metal employed is preferably finely divided, preferably powdered, zinc, magnesium or manganese, or mixtures of two or more thereof.

During the reductive coupling reaction, the concentrations of the various reactant materials and their ratios as set forth above will necessarily change and it is preferred for continuous operations that their concentrations be maintained at least within the specified broad ranges by addition of these reactants to the reaction system as is necessary.

It is also noted with respect to the above stated reaction conditions, that the temperatures employed will be dictated to a degree by the particular reactants employed, and also by the size and design of the equipment. For example, the thermal stability of these materials must be considered and any exotherm monitored to prevent degradation or excessive side reactions. The pressure of the reductive coupling reaction systems need only be ambient, and lower or higher pressures give no significant enhancement to the reaction and typically are not warranted.

In regard to the isolation and work up of the coupled product, the procedure generally involves the following sequence of steps: aqueous quench, filtration, aqueous washes, distillation or concentration, and recrystallization. The crude product obtained by this work up typically contains about 500 to 750 ppm of nickel, in such forms as polymeric nickel phosphine complexes and discrete monomeric complexes with the bidentate ligand, both types of complexes containing nickel in the 0 and +2 oxidation states.

One of skill in the art can readily determine various means to reduce the nickel content of the coupling reaction mixture, e.g., extraction, recrystallization, chromatographic methods and the like. When extraction is employed, extracting solutions useful for this purpose include caustic/-cyanide, ethylenediaminetetraacetic acid, ammonium hydroxide, dimethyl glyoxime, concentrated hydrochloric acid, oxalic acid, and the like.

The presently preferred technique for separating the nickel complexes from bidentate ligand is by recrystallization from a suitable solvent, such as, for example, acetone, methyl ethyl ketone, methanol/-acetone, ethanol/acetone, and the like.

The reactant which is subjected to reductive coupling in accordance with the present invention can be prepared in a variety of ways. For example, a metal halide reagent of the formula:

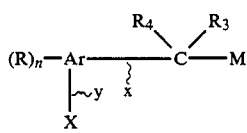

the x bonds and the y bonds are attached to adjacent carbon atoms on the ring structures;

and wherein M is selected from the group consisting of Li, MgX, Na, K, Cd, Zn and Ca can be contacted with a compound of the formula:

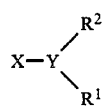

wherein X is a halogen, under conditions suitable to form the desired reactant.

The reaction for preparing the desired reactant is typically carried out in the presence of a solvent such as diethyl ether, tetrahydrofuran (THF), THF/toluene mixtures, aprotic dialkyl ethers, ethylene glycol dialkyl ethers, particularly ethylene glycol dimethyl-, dipropyl-, and dibutyl-ethers; most preferably diethyl ether. The reaction is carried out at a temperature in the range of about 0° C. up to 60° C., preferably at about the reflux temperature of the solvent. Reaction pressure is not critical, and is preferably about one atmosphere.

The molar ratio of the metal halide reagent to the diorgano-Group V halide reactant can vary widely, with a ratio of essentially 1/1 typically being employed since no excess of either is necessary.

Alternatively, the reactant can be prepared by contacting a halobenzyl compound of the formula:

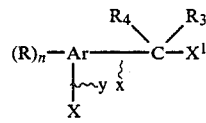

wherein $X^1$ is a halogen or appropriate leaving group, e.g., tosylate, mesylate, brosylate, and the like; and the x bonds and the y bonds are attached to adjacent carbon atoms on the ring structures;

with a diorganometallo-Group V compound of the formula:

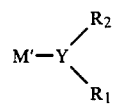

wherein M' is selected from the group consisting of lithium, sodium, potassium, magnesium, calcium, zinc and cadmium.

This contacting is preferably carried out in an anhydrous, aprotic solvent, such as, for example, an ether (e.g., diethyl ether, tetrahydrofuran), aromatic hydrocarbon (e.g., toluene, xylene), as well as mixtures of any two or more thereof.

It is preferred, for ease of manipulation, that the metallo moiety be preformed in a separate reaction vessel, and thereafter contacted with the halobenzyl compound.

One example of this synthetic approach is the reaction of a strong base, such as n-butyl lithium, with a secondary organophosphine, e.g., diphenyl phosphine.

Alternatively, the metallo moiety can be formed by the reductive cleavage of a tertiary organophosphine employing dissolving metal reactions. For example, sodium diphenylphosphide can be produced by treating chlorodiphenylphosphine in toluene with sodium metal; or lithiodiphenylphosphine can be prepared by treating triphenylphosphine in tetrahydrofuran with lithium metal.

As another alternative, a halobenzyl-Group V oxide of the structure:

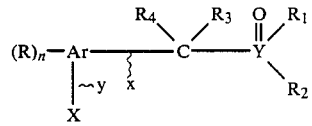

can be prepared, then reduced to give the desired reactant. This is an especially attractive alternative when the desired precursor compounds are not readily available. Thus, dialkyl halobenzylphosphines can readily be prepared in this manner. For example, one equivalent of diethyl phosphite can be treated with three equivalents of benzylmagnesium chloride to produce the magnesium salt of dibenzylphosphine oxide. The secondary phosphine oxide can also be formed by the reaction of a strong base (e.g., n-butyl lithium) with a secondary phosphine oxide. Reaction of the resulting organometallic compound with 2-chlorobenzyl chloride produces dibenzyl-(2-chlorobenzyl)phosphine oxide which can then be reduced to the phosphine with an appropriate reducing agent, such as, for example, lithium aluminum hydride or trichlorosilane.

The following examples will further illustrate the invention:

EXAMPLE 1

Preparation of 2-Chlorobenzyldiphenylphosphine (a) To a suspension of magnesium turnings (15.50 grams, 0.636 mole) in diethyl ether (500 mL) under nitrogen in a three-necked flask equipped with a reflux condenser, addition funnel, and mechanical stirrer was added a solution of 2-chlorobenzylchloride (93.0 grams, 0.578 mole) in diethyl ether (100 mL). The addition was made at a rate such that a gentle reflux was maintained throughout the addition. Upon completion of the addition, the reaction was heated to reflux for an additional 0.5 hour to give a solution of the desired Grignard reagent. This preparation of the Grignard reagent is typical and other conditions for such preparation are known to the art and may be employed in connection with the present invention.

(b) Chlorodiphenylphosphine (115.84 grams, 0.525 mole) in diethyl ether (200 mL) was added dropwise with vigorous stirring to the above solution of the Grignard reagent at a rate such that a moderate reflux was maintained. Upon completion of the addition, the reaction was refluxed for 1 hour, cooled to ambient temperature, and quenched with concentrated HCl (50 mL) in 400 mL of water. The quench was initially highly exothermic and required a careful dropwise addition. After all the solids were digested, the layers were separated and the organic layer washed with water (2×200 mL). The wash mixtures were filtered to remove residual solid contaminants, the layers separated, and the final organic layer stripped to dryness to give 167 grams of crude product as a crystalline solid. This product was analyzed and found to be sufficiently pure to use without further purification.

EXAMPLE 2

Preparation of BISBI From 2-Chlorobenzyldiphenylphosphine Using Magnesium as the Reducing Metal To a nitrogen purged 50-mL flask was charged 2-chlorobenzyldiphenylphosphine (6.21 grams, 0.02 mole), magnesium powder (1.46 grams of −325 mesh, 0.06 mole), anhydrous nickel chloride (0.13 gram, 0.001 mole), and dimethylformamide (20 mL). The reaction system was heated to 120° C. and held at that temperature for 8 hours. The mixture was then cooled to room temperature and quenched by the addition of ether (50 mL) and water (50 mL). The solids were removed by filtration and the layers separated. The organic phase was successively washed, with layer separation, with 1N hydrochloric acid (1×50 mL), with 5 percent sodium bicarbonate (1×25 mL), and with saturated NaCl solution (1×50 mL). The final organic layer was stripped to give the crude product which was then dissolved in acetone (50 mL) and filtered to remove polymeric nickel species. The acetone solution was concentrated to 10 mL, diluted with methanol (25 mL), chilled to 0° C. and the product filtered therefrom. The product was dried under vacuum to give 3.31 grams (60 percent of theory) of BISBI which was pure by phosphorus 31 NMR.

EXAMPLE 3

Preparation of BISBI From 2-Chlorobenzyldiphenylphosphine Using Zinc as the Reducing Metal To a three-neck, one-liter flask equipped with reflux condenser, thermometer, and stirring bar was added 2-chlorobenzyldiphenylphosphine (114.9 grams, 0.37 mole), anhydrous nickel bromide (4.05 grams, 0.0185 mole), zinc (72.57 grams of −325 mesh powder, 1.11 mole), and dimethylformamide (300 mL). The reaction mixture was heated with stirring to 120° C. whereupon the reaction exothermed to approximately 150° C. The exotherm was controlled by external cooling. After the initial exotherm subsided, the reaction mixture was maintained at 120° C. for 2 hours and the disappearance of starting material was monitored by gas chromatography. The reaction mixture was cooled to room temperature, ether (300 mL) and water (200 mL) were then added. The reaction mixture was then filtered, mainly to remove the excess zinc. The ether and aqueous layers were separated and the initial organic ether layer or phase was washed successively, with separation, with water (200 mL), with 5 percent HCl (200 mL), with 5 percent sodium bicarbonate (200 mL), and again with water (200 mL). All of the aqueous phases except the bicarbonate phase were combined and backwashed with a 1/1 mixture of hexane and ether (200 mL total). The separated organic phase was then combined with the initial organic phase. The combined (final) organic phase was concentrated to give a crude product which solidified and was triturated in hexane (400 mL) and ether (30 mL) to give a powdery yellow solid. The solid was dissolved in hot ethanol/acetone (600 mL of a 5/1 mixture), filtered hot, and allowed to slowly cool to room temperature. This crystallization mixture was then cooled to 0° C., filtered and the cake rinsed with ice cold ethanol to give a white solid which was dried in vacuo to give 74.5 grams of BISBI. This product was analyzed and found to contain 18 ppm of nickel. The liquor was concentrated and chilled to obtain a second crop of crystals amounting to 5.5 grams. The overall yield of BISBI was 80.0 grams which is 80 percent of the theoretical yield.

EXAMPLE 4

2,2'-Bis(dibenzylphosphinomethyl)-1,1'-biphenyl Dioxide

Dibenzylphosphine oxide (6.93 grams, 30.1 mmol) and THF (100 ml) were placed in a 300-ml three-necked flask and cooled at −40° C. under nitrogen. n-Butyllithium (18.84 ml of a 1.6M solution in hexane, 30.1 mmol) was added dropwise from an addition funnel over about 10 minutes and the resulting yellow solution was stirred for one hour at −30° C. to −35° C. 2,2'-Bis(bromomethyl)-1,1'-biphenyl (5.00 grams, 14.7 mmol) in THF (20 ml) was added dropwise to the cold solution. When the addition was complete, the solution was warmed to room temperature and was then heated at reflux for 1.5 hours. Saturated aqueous NH$_4$Cl was added and the layers were separated. The aqueous layer was extracted twice with diethyl ether. The combined organic solution was washed with saturated aqueous NaCl. The organic solvent was evaporated on a steam bath under a stream of nitrogen to give a light brown solid. The product was recrystallized from acetone to give a first crop of 3.57 grams (38% yield) of white solid, melting point 203° to 205° C. No attempt was made to recover a second crop.

$^1$H NMR (CDCl$_3$): δ2.07–3.08 (complex, 12H, benzylic); 6.57–7.47 (complex, 28H, aromatic). $^{31}$p NMR (CDCl$_3$): δ−43.

EXAMPLE 5

2,2'-Bis(dibenzylphosphinomethyl)-1,1'-biphenyl

Chlorotrimethylsilane (4.1 ml, 32.2 mmol) was added to lithium aluminum hydride (1.22 grams, 32.2 mmol) in THF (20 ml) at −72° C. The mixture was removed from the cold bath, stirred two hours, and then cooled again at −35° C. A suspension of the above 2,2'-bis(-dibenzylphosphinomethyl)-1,1'-biphenyl dioxide (3.40 grams, 5.32 mmol) in THF (45 ml) was added by cannula. The mixture was stirred 0.5 hour at −30° C., then overnight at room temperature. The reaction mixture was cooled in an ice bath and quenched by the successive, dropwise addition of water (1.2 ml), 15% aqueous NaOH (1.2 ml) and water (3.6 ml). The resulting mixture was filtered, and the solid was washed with diethyl ether. The filtrate was evaporated on the steam bath under a stream of nitrogen. The residual solid was heated in ethanol, then cooled and filtered to give 2.00 grams (62% yield) of white solid, melting point 163° to 167° C.

$^1$H NMR (CDCl$_3$): δ2.43 (s, 12H, benzylic); 6.50–7.17 (complex, 28H, aromatic). $^{31}$P NMR (CDCl$_3$): δ+9.5.

It is thus seen that the present invention provides a new synthetic route to economically valuable organophosphine ligands, particularly, 2,2'-bis(diphenylphosphinomethyl)-1,1'-biphenyl (BISBI) by the reductive dimerization of 2-halobenzyldiorganophosphines. The 2-halobenzyldiorganophosphines can be prepared by a variety of techniques, e.g., reaction of the Grignard reagent of 2-halobenzyl halide with halodiorganophosphine using standard procedures. In Example I, the intermediate reactant was prepared in sufficiently pure form that it could be used without further purification. Another advantage of this route is that the product organophosphine ligand is readily available in high yield.

The invention has been described in detail with particular reference to preferred embodiments thereof, but it will be understood that variations and modifications can be effected within the spirit and scope of the invention.

I claim:

1. A process for preparing a bidentate ligand of the formula:

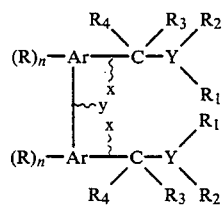

wherein:
each Ar is independently selected from aromatic ring compounds having 6 up to 14 carbon atoms;
the x bonds and the y bonds are attached to adjacent carbon atoms on the ring structures;
each R, when present as a substituent, is independently selected from alkyl, alkoxy, aryloxy, aryl, aralkyl, alkaryl, alkoxyalkyl, cycloaliphatic, halogen, alkanoyl, alkanoyloxy, alkoxycarbonyl, carboxyl, cyano or formyl radicals;
n is a whole number in the range of 0–4 where Ar is phenyl; 0–6 where Ar is naphthyl; and 0–8 where Ar is phenanthryl or anthracenyl;
each R$_1$ and R$_2$ is independently selected from alkyl, aryl, aralkyl, alkaryl or cycloaliphatic radicals, or substituted derivatives thereof, wherein the substituted derivatives are selected from ethers, amines, amides, sulfonic acids, esters, hydroxyl groups or alkoxy groups;
each R$_3$ and R$_4$ is independently selected from hydrogen and the R$_1$ substituents;
each of the above alkyl groups or moieties is a straight or branched chain of 1–20 carbons;
each aryl group contains 6–10 ring carbons;
each cycloaliphatic group contains from 4–8 ring carbons; and
each Y is independently selected from the elements N, P, As, Sb and Bi;
said process comprising:
(i) contacting a reagent having the structure:

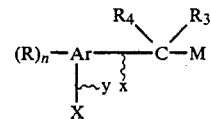

wherein X is a halogen;
M is selected from the group consisting of Li, MgX, Na, K, Cd, Zn and Ca; and
the x bonds and the y bonds are attached to adjacent carbon atoms on the ring structures;
with a compound of the formula:

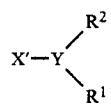

wherein X' is halogen or a suitable leaving group under conditions suitable to form a reactant of the formula:

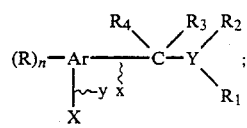

then
(ii) maintaining a redox reaction system comprising
(a) said reactant,
(b) a polar, aprotic solvent,
(c) a nickel compound, and
(d) a reducing agent, which has a sufficient reducing potential to promote the reduction of Ni(II) to Ni(O), at a temperature and for a time sufficient to form said ligand.

2. The process of claim 1 wherein the reactant has the formula:

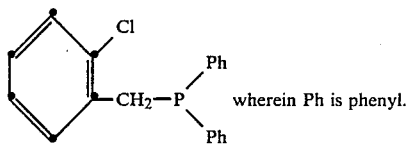 wherein Ph is phenyl.

3. The process of claim 1 wherein the reducing agent is selected from finely divided Zn°, Mg° or Mn° and is present with respect to the nickel compound in a molar ratio of reducing agent to nickel compound in the range of about 5/1 up to 1000/1.

4. The process of claim 1 wherein said redox system is maintained at a temperature in the range of about 50 up to 200° C.

5. The process of claim 1 wherein said redox system is maintained at a temperature in the range of about 110° up to 140° C.

6. The process of claim 1 wherein M is MgX.

7. The process of claim 6 wherein X is chlorine, $R_3$ and $R_4$ are H, Ar is phenyl, n is zero, and each $R^1$ and $R^2$ is independently selected from the group consisting of phenyl, benzyl, and alkyl radicals having 1–6 carbon atoms.

8. The process of claim 6 wherein the reactant has the formula:

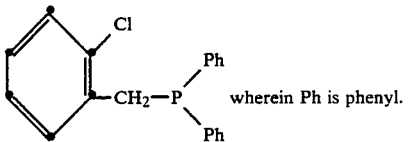 wherein Ph is phenyl.

9. The process of claim 1 wherein the molar ratio of the reducing agent to the nickel compound falls within the range of about 10/1 up to 400/1, and the molar ratio of the reactant to the nickel compound falls in the range of about 2/1 up to 100/1.

10. The process of claim 1 wherein the molar ratio of the reducing agent to the nickel compound falls within the range of about 25/1 up to 100/1, and the molar ratio of the reactant to the nickel compound falls in the range of about 5/1 up to 40/1.

11. The process of claim 1 wherein the reducing agent is an electrolytic cell.

* * * * *